(12) United States Patent
Sana et al.

(10) Patent No.: US 9,532,735 B2
(45) Date of Patent: Jan. 3, 2017

(54) APPARATUS AND METHOD FOR WIRELESS MONITORING USING ULTRA-WIDEBAND FREQUENCIES

(71) Applicant: KING ABDULLAH UNIVERSITY OF SCIENCE AND TECHNOLOGY, Thuwal OT (SA)

(72) Inventors: Furrukh Sana, Thuwal (SA); Tarig Ballal Khidir Ahmed, Thuwal (SA); Tareq Al-Naffouri, Thuwal (SA); Ibrahim Hoteit, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 14/522,005

(22) Filed: Oct. 23, 2014

(65) Prior Publication Data
US 2015/0112220 A1    Apr. 23, 2015

Related U.S. Application Data

(60) Provisional application No. 61/894,840, filed on Oct. 23, 2013.

(51) Int. Cl.
*A61B 5/02*    (2006.01)
*A61B 5/113*   (2006.01)
*G06F 19/00*   (2011.01)
*A61B 5/05*    (2006.01)
*H04B 1/7163*  (2011.01)
*A61B 5/00*    (2006.01)

(52) U.S. Cl.
CPC ............... *A61B 5/113* (2013.01); *A61B 5/05* (2013.01); *G06F 19/3418* (2013.01); *H04B 1/7163* (2013.01); *A61B 5/7207* (2013.01)

(58) Field of Classification Search
CPC ......... A61B 5/05; A61B 5/113; A61B 5/7207; G06F 19/3418; H04B 1/7163
See application file for complete search history.

(56) References Cited

U.S. PATENT DOCUMENTS

| 5,361,070 A | * | 11/1994 | McEwan | ............... | A61B 5/0507 342/21 |
| 2002/0175850 A1 | * | 11/2002 | Barnes | ................ | G01S 13/0209 342/22 |
| 2009/0222226 A1 | * | 9/2009 | Baraniuk | ............... | H03M 13/11 702/66 |

\* cited by examiner

*Primary Examiner* — George Manuel
(74) *Attorney, Agent, or Firm* — Steptoe & Johnson LLP

(57) ABSTRACT

A system for and a method of wirelessly monitoring one or more patients can include transmitting ultra-wideband pulses toward the one or more patients, receiving ultra-wideband signals, and sampling the ultra-wideband signals. Sampling the ultra-wideband pulses can be performed with a sample rate that is less than the Nyquist rate. Impulse response can be estimated and/or recovered by exploiting sparsity of the impulse response.

29 Claims, 11 Drawing Sheets

APPARATUS AND METHOD FOR WIRELESS MONITORING USING ULTRA-WIDEBAND FREQUENCIES

CLAIM OF PRIORITY

This application claims priority to U.S. Provisional Application No. 61/894,840, filed on Oct. 23, 2013, which is incorporated by reference in its entirety.

TECHNICAL FIELD

The present invention is directed to a system and method for wirelessly monitoring biological functions using ultra-wideband frequencies and estimating ultra-wideband channel impulse response.

BACKGROUND

Respiratory parameters such as respiratory rate and amplitude can provide vital information about a person's state of health. Diagnosis of several illnesses and disorders, for example sleep apnea, bradydysrhythmia, and/or bradycardia, can be based on the analysis of recordings of respiratory movements while the patient is asleep. Such recordings are often performed overnight in isolated hospital environments using polysomnography during which the patient is required to sleep under conditions of restricted motion while connected to numerous devices and electrodes. Furthermore, for continuous disorders such as sleep apnea, studies might be repeated several times to assess the effectiveness of treatment. The associated costs and discomfort can be high for the patient.

Patients at a risk of undergoing a sudden respiratory death risk have traditionally been monitored by electrocardiography ("ECG"). ECG monitoring can capture tachy dysrhythmias that can be a cause of preventable sudden respiratory death. Historically, it was believed that this was the most cost effective way to detect preventable sudden respiratory death of patients early. However, some patients experience bradydysrhythmia in the ten minutes prior to the calling of a code blue. Bradydysrhythmia is associated with hypoxia, which indicates that respiratory arrest, and not cardiac arrest, may be resulting in a respiratory arrest/death event in these patients. ECG monitoring may not detect the respiratory arrest early enough to allow for successful resuscitation. Respiratory monitoring technology exists. One approach currently available for monitoring respiratory arrest is pulse oximetry. Additionally, respiratory rate monitors, expired and/or transcutaneous $CO_2$ monitoring, and air flow recording devices have also been used. Current respiratory rate and $CO_2$ monitoring devices, however, are not always reliable nor do they produce reproducible data in the awake and active patient. $CO_2$ monitoring can also be expensive and difficult to calibrate. Moreover, as with monitoring for sleep apnea, oximetry monitors rely on connecting the patient to numerous devices and/or electrodes.

As such, a non-invasive non-contact technique that offers low cost and reliable monitoring of respiratory movements is needed.

Ultra-wideband (UWB) technology offers the possibility of monitoring respiratory movements non-invasively and wirelessly. Indeed, UWB technology has been increasingly studied for ranging and imaging applications in medical environments. Compared with narrowband technologies, UWB offers the large bandwidth suitable for high-resolution ranging while operating in a low-power regime. UWB signals create no or minimal interference with other sensitive equipment in the surroundings, which can be of critical importance in medical environments. Although applications such as the monitoring of respiratory movements and diagnosis of the sleep apnea have been previously considered, they have been limited by several practical challenges. For example, earlier studies focus on estimating only vital signs, such as breathing and heart rates. Diagnosis of many illnesses and disorders, however, requires continuous monitoring of the respiratory amplitude to detect abnormalities in the breathing pattern. This requires accurate tracking of respiratory signals with high range resolution.

Monitoring via UWB can pose several challenges including multipath effects, low signal-to-noise ratios (SNR), and high sampling rate requirements. These challenges can be compounded by non-isolated and possibly time-variant environments. Some of these issues have been addressed, but no comprehensive scheme has been suggested that simultaneously deals with all of these issues. For example, earlier techniques have been based on time-of-arrival (TOA) methods that rely on accurate identification of the direct path component. However, in a multipath environment, a direct path may not exist or it may not be the strongest signal. Some schemes assume that the multipath environment is known and time-invariant, but this assumption is not practical in a non-isolated environment. Other schemes attempt to identify the direct path, which is a challenging task and adds additional complexity to the problem.

To improve the effective SNR, a technique has been suggested that utilizes the redundant information available in the sub-peaks of the received signal. See, for example, Lai et al., "Wireless Sensing of Human Respiratory Parameters by Low-Power Ultrawideband Impulse Radio Radar." The effectiveness of this technique is, however, limited. A more widely used technique in typical UWB systems is to utilize multiple pulse transmissions to build a stronger received signal profile through averaging. Because of their large bandwidths, UWB systems require high sampling rates to recover information accurately from the received signals. A solution to this problem has not been previously offered. Further, the techniques rely on equipment such as the digital oscilloscope as their front-end hardware to achieve good tracking accuracy. Dependence on such complex hardware can be a major bottleneck in any efficient and cost-effective UWB solution.

SUMMARY

In an aspect, a monitoring system for assessing one or more patients can include a pulse generator, an ultra-wideband transceiver, a sampler, and a processor in communication with the pulse generator, the transceiver, and/or the sampler. The pulse generator can be configured to generate ultra-wideband pulses. The ultra-wideband transceiver can be configured to transmit ultra-wideband pulses, and the transmission can be directed toward the one or more patients. The transceiver can be further configured to receive ultra-wideband signals from the one or more patients. The ultra-wideband pulses can be described by their Nyquist sampling rate. In other words, the recovery of the ultra-wideband signal at a receiver can be subject to the Nyquist rate of sampling. The sampler can be configured to sample the ultra-wideband signals at a sample rate less than the Nyquist rate.

In some embodiments, the processor can be configured to analyze a number of received and/or sampled pulses. The number of sampled pulses can be substantially equivalent to the ratio of the Nyquist rate to the sample rate. The sampler and/or the processor can subsample the signals. Subsampling the signals can further include calculating a differential signal to remove background noise and/or clutter.

In other embodiments, the ultra-wideband pulses can be separated by a time interval of $T_p$. A condition can be applied such that the subsampling ratio, N, conforms with $L_p=mN-1$, and where m is an integer and $L_p=T_pf_N$, in other words, the number of samples in the pulse interval $T_p$. The processor can be configured to execute a greedy algorithm to estimate an impulse response based on a sparse matrix.

In some embodiments, an impulse response can be estimated and/or recovered. Impulse response can be estimated and/or recovered by exploiting sparsity of the impulse response.

In yet other embodiments, the processor can be configured to monitor one or more biological functions. The biological functions can include respiration and/or heart rate. The processor can be configured to monitor movement. The movement can include small rhythmic movements associate with respiration and/or heart beats. The movement can include larger movements associated with bodily adjustments, convulsions, seizures, and the like.

In an aspect, a method of wirelessly monitoring one or more patients can include transmitting ultra-wideband pulses toward the one or more patients, receiving ultra-wideband signals, and sampling the ultra-wideband signals. The ultra-wideband pulses can be described by their Nyquist rate. The sampling can be performed with a sample rate that is less than the Nyquist rate.

In some embodiments, the method can further include analyzing a number of sampled pulses. The number of sampled pulses can be substantially equivalent to the ratio of the Nyquist rate to the sample rate. The method can include calculating a differential signal. The method can also include removing background noise and/or clutter.

In other embodiments, the ultra-wideband pulses can be separated by a time interval of $T_p$. A condition can be enforced such that the subsampling ratio, N, conforms with $T_p=mN-1$, where m is an integer. The method can further include executing a greedy algorithm. The greedy algorithm can be utilized to estimate an impulse response based on a sparse matrix.

In some embodiments, an impulse response can be estimated and/or recovered. Impulse response can be estimated and/or recovered by exploiting sparsity of the impulse response.

In yet other embodiments, the method can further include monitoring one or more biological functions. The biological functions can include respiration and/or heart rate. The processor can be configured to monitor movement. The movement can include small rhythmic movements associate with respiration and/or heart beats. The movement can include larger movements associated with bodily adjustments, convulsions, seizures, and the like.

In some embodiments, the method can further include calculating a differential signal. The method can include estimating an impulse response. The ultra-wideband signals can be reflections of and/or scattered signals from the ultra-wideband pulses. The method can further include estimating a time of travel of the ultra-wideband pulses and the ultra-wideband signals. The method can include calculating a position as a function of time to determine one or more biological functions.

In an aspect, a computer can have a non-transitory computer readable medium comprising a program for monitoring a patient. The computer and program can be configured to execute several procedures, including transmitting to the patient a sequence of N pulses, receiving signals based on the sequence of N pulses, and subsampling the signals. The N pulses can each have a duration of $T_w$ and be separated from each other by a period of $T_p$. The signals can be subsampled at a sample rate defined by the Nyquist rate reduced by a factor of N. Further, N and $L_p$ can be subject to the condition $L_p=mN-1$, where m is an integer and $L_p$ can be defined as $L_p=T_pf_N$, in other words, the number of samples in the pulse interval $T_p$, where $f_N$ is the Nyquist frequency.

In some embodiments, subsampling the signals can further include calculating a differential signal to remove background noise and/or clutter.

In some embodiments, the computer and program can be further configured to remove background noise and/or clutter, estimate an impulse response, and track respiratory movement. The sequence of N pulses can comprise ultra-wideband pulses. The sequence of N pulses can comprise ultrasonic pulses.

BRIEF DESCRIPTION OF THE DRAWINGS

The following drawings form part of the present specification and are included to further demonstrate certain aspects of systems and methods described herein, which may be better understood by reference to one or more of these drawings in combination with the detailed description of specific embodiments presented herein.

DETAILED DESCRIPTION

Exemplary embodiments described, shown, and/or disclosed herein are not intended to limit the claims, but rather, are intended to instruct one of ordinary skill in the art as to various aspects of the invention. Other embodiments can be practiced and/or implemented without departing from the scope and spirit of the claimed invention.

In addition to the needs discussed above, there is a need for a low-complexity UWB technique for monitoring respiratory movements of a human subject. The low-complexity solution should provide reliable tracking performance in a realistic environment and should mitigate effects of multipaths in a time varying environment. Unlike UWB schemes proposed previously in the literature, techniques discussed herein can reduce the required sampling rate significantly, which can lower complexity and ease hardware requirements. The problem can be formulated from a sparse signal estimation perspective using a Bayesian framework, which can help in achieving good tracking performance against low SNR values. Present embodiments provide robust solutions to the above-mentioned challenges while maintaining low levels of complexity.

Figure 1:
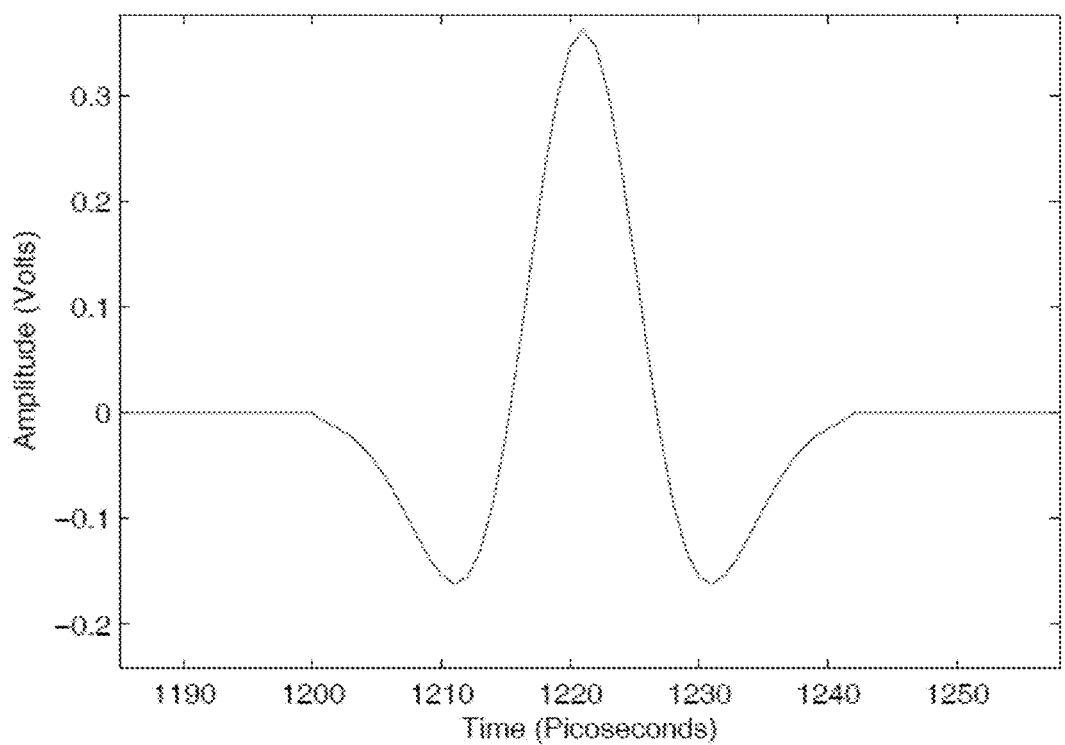
FIG. 1 depicts an exemplary ultra-wideband pulse.

FIG. 1 shows the typical shape of a transmitted pulse in a UWB system. The pulse in the figure is a second derivative Gaussian pulse with its mathematical expression given by:

$$p_{tx} = \frac{1-((t-\mu)/\sigma^2)}{\sqrt{2\pi}\,\sigma}\exp(-(t-\mu)^2/2\sigma^2), \quad (1)$$

where $\mu = T_w/2$, $\sigma = T_w/7$ and $T_w$ is the pulse width.

As mentioned above, despite its advantages, wireless monitoring through UWB poses several practical challenges. Because of their low power profiles under FCC regulations, prior UWB systems could not be expected to operate in regimes with high signal-to-noise ratios (SNR). A typical technique to improve the effective SNR is to transmit multiple pulses within a single measurement time window and average the received signals over that period. Performance in low SNR regimes, however, can be improved by exploiting the sparsity inherent in the UWB channel impulse response and/or through its estimation using, for example, a Bayesian framework. Details on how to formulate the respiratory movement tracking problem using UWB signals as a sparse signal estimation problem are further discussed herein.

Importantly, it should be noted that a multiple pulse transmission technique can be useful for relaxing the sampling rate constraint. A respiratory signal typically has low peak-to-peak amplitude in the range of 4 to 12 mm. Hence, variations are small and can be tracked accurately by utilizing high-resolution pulses. The relationship between the range resolution $\delta r$ and the pulse width is given by:

$$\delta r = \frac{T_w c}{8} \quad (2)$$

where $T_w$ is the width of the pulse in the time domain and c is the speed of the electromagnetic waves. The required Nyquist sampling rate is given by:

$$f_N = \frac{4}{T_w} \quad (3)$$

More generally, it can be stated that $f_N$ is directly proportional to $1/T_w$, where the constant of proportionality is dependent on the shape of the ultra-wideband pulse considered, in other words:

$$f_N \propto \frac{1}{T_w}$$

Obtaining a range resolution of 2 mm, for example, would require a pulse width of 50 picoseconds. This translates into a Nyquist sampling rate of 80 GHz, which is generally too high for practical purposes. Present embodiments can allow recovery of UWB signals while operating at sub-Nyquist rates.

Figure 2:
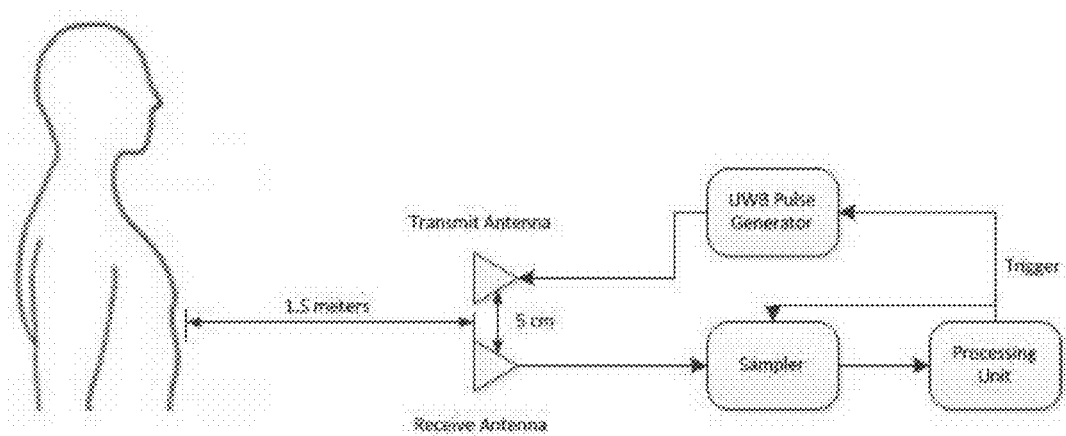
FIG. 2 illustrates an exemplary system and the positioning of the transceiver in relation to a human subject.

An exemplary embodiment is shown schematically in FIG. 2. The system can include a transceiver, which includes a transmitting antenna component and a receiving antenna component. Either or both of the transmitting and receiving antenna components can include multiple-antenna systems, such as, for example, a multiple-input and multiple-output (MIMO) antenna array. The antenna components can include adaptive array antennas or other smart antenna configurations. The antennas can further be configured to provide a favored direction and/or a favored polarization to, for example, extend the operating range of the system and/or improve signal reception.

In an alternative embodiment of FIG. 2, the transceiver can be a sonic or ultrasonic transceiver. The transmitter can include a sonic or ultrasonic transmitter. The receiver can include a sonic or ultrasonic sensor for detecting echoes.

The exemplary system can further include a pulse generator. The pulse generator can generate ultra-wideband signals which can be sent to the transmitter and transmitted toward a patient, shown as approximately 1.5 meters from the transceiver in FIG. 2. A sampler can further be included to sample signals received by the receiver. A processor can be in communication with both the pulse generator and the sampler and can provide control instructions to these components. For example, the processor can provide a trigger for the pulse generator that causes a train of N pulses to be sent to the transmitter. The processor can further instruct the sampler to sample signals over an appropriate timeframe in order to sample the N signals. The processor can perform further functions and algorithms discussed below.

Figure 13:
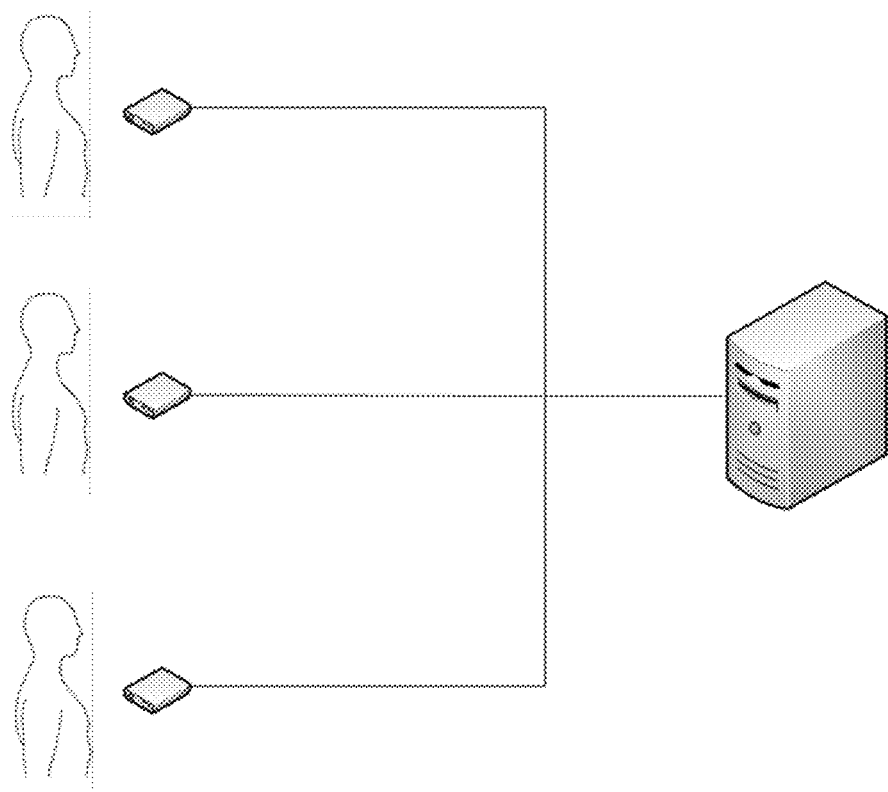
FIG. 13 illustrates an exemplary embodiment for use with a plurality of patients.
Figure 14:
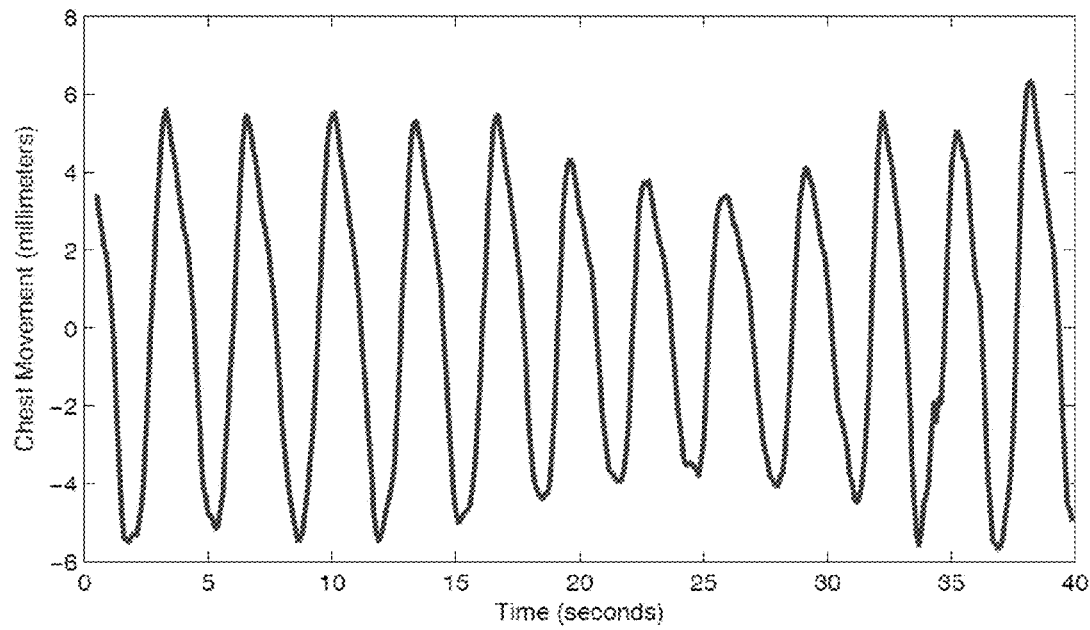
FIG. 14 depicts an exemplary pre-recorded respiratory signal.
Figure 15:
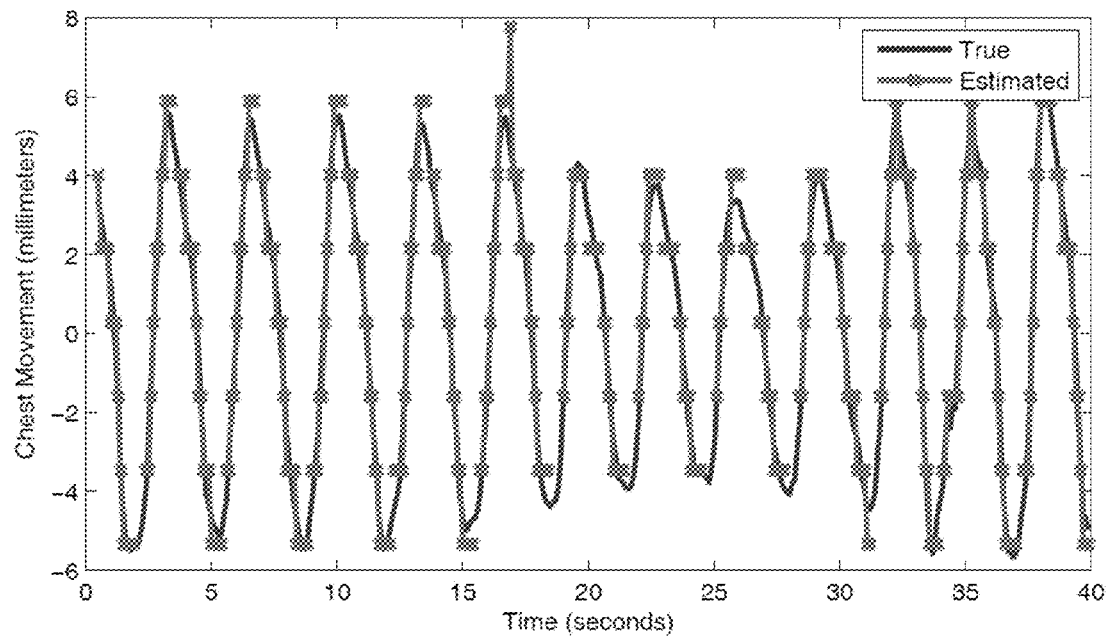
FIG. 15 depicts signal reconstruction performance at 15 dB SNR with a Nyquist sampling rate of 80 GHz.
Figure 16:
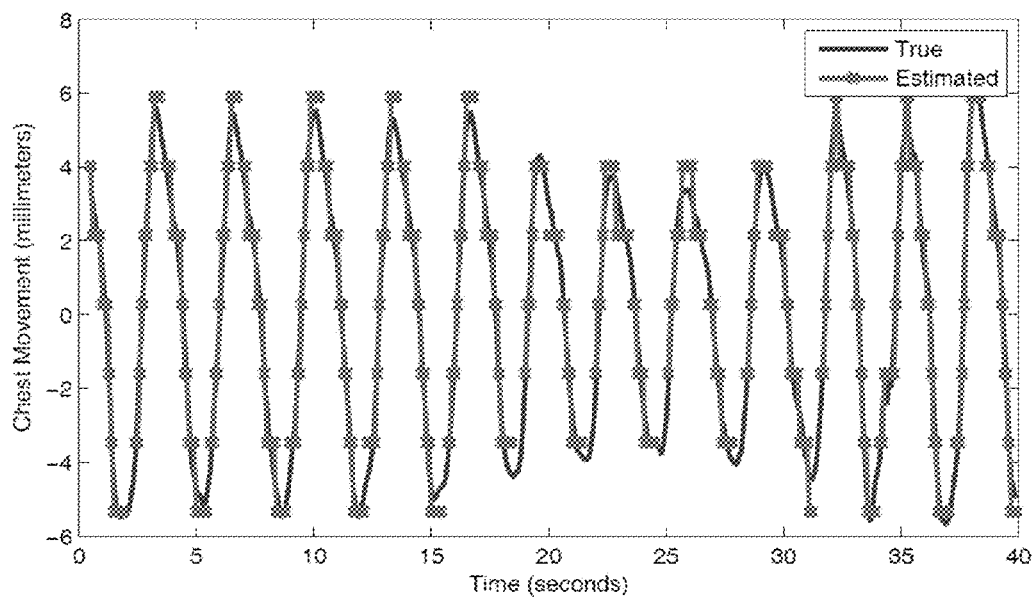
FIG. 16 depicts signal reconstruction performance at 15 dB SNR with a sub-Nyquist sampling rate of 2.1 GHz.
Figure 17:
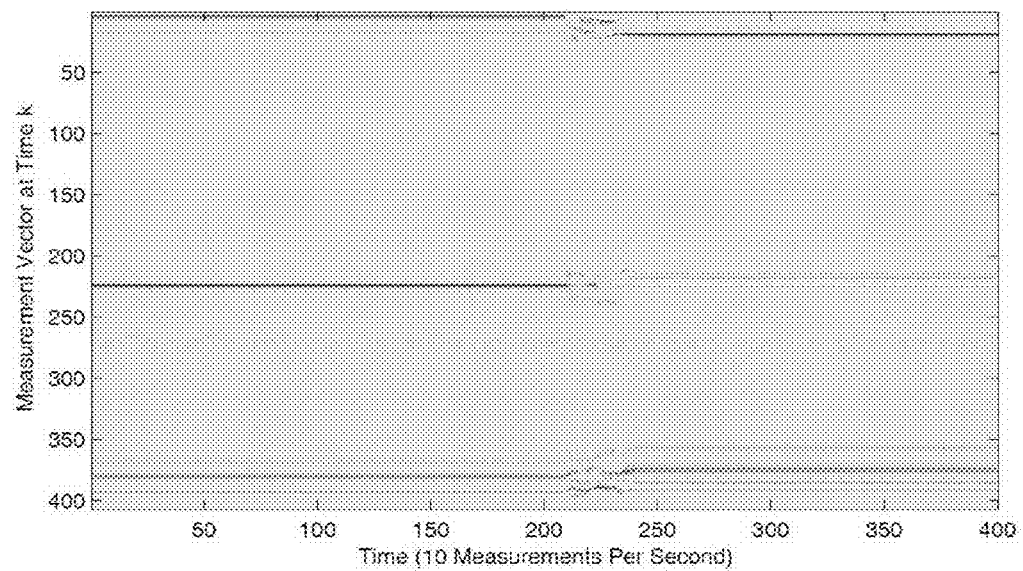
FIG. 17 depicts measurement vectors in an environment with a slowly changing background.
Figure 18:
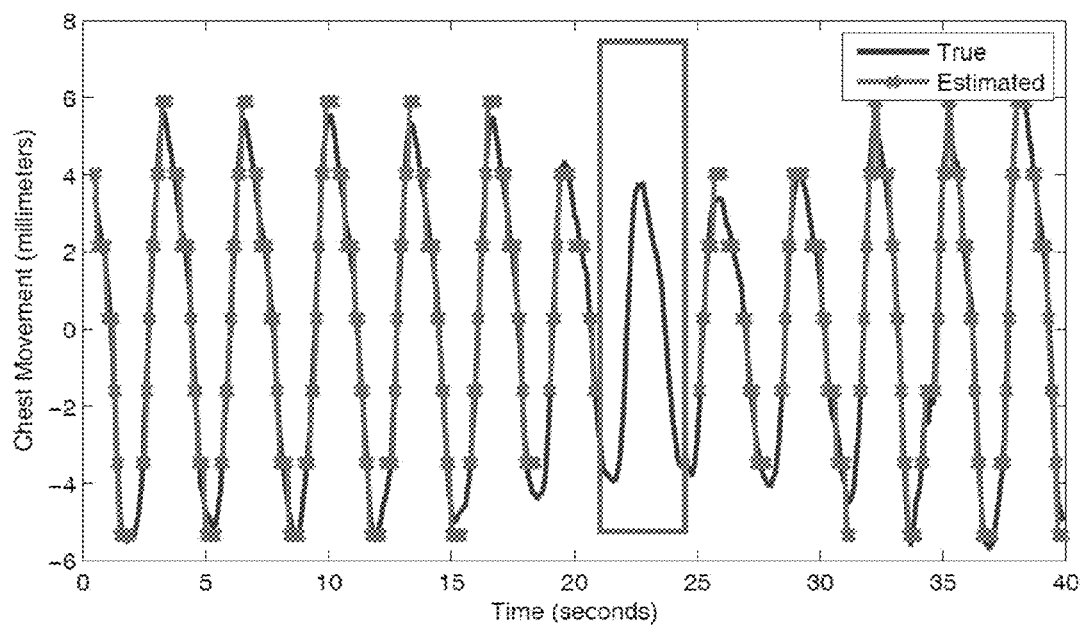
FIG. 18 depicts tracking performance in an environment with a slow-varying background at 15 dB SNR and with a sub-Nyquist sampling rate of 2.1 GHz.
Figure 19:
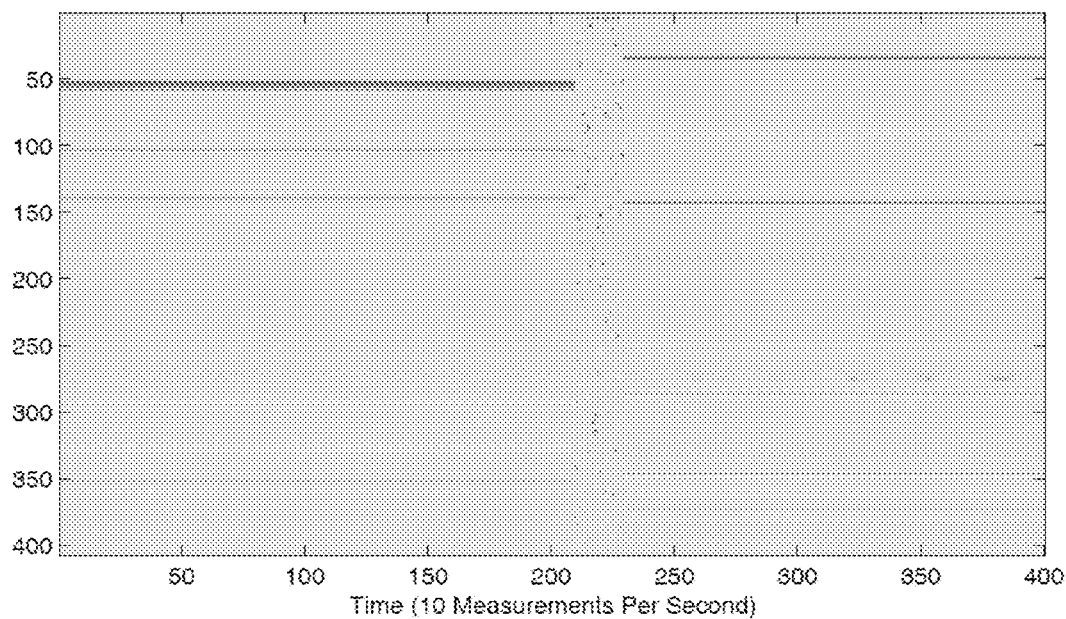
FIG. 19 depicts measurement vectors in an environment with a quickly changing background.
Figure 20:
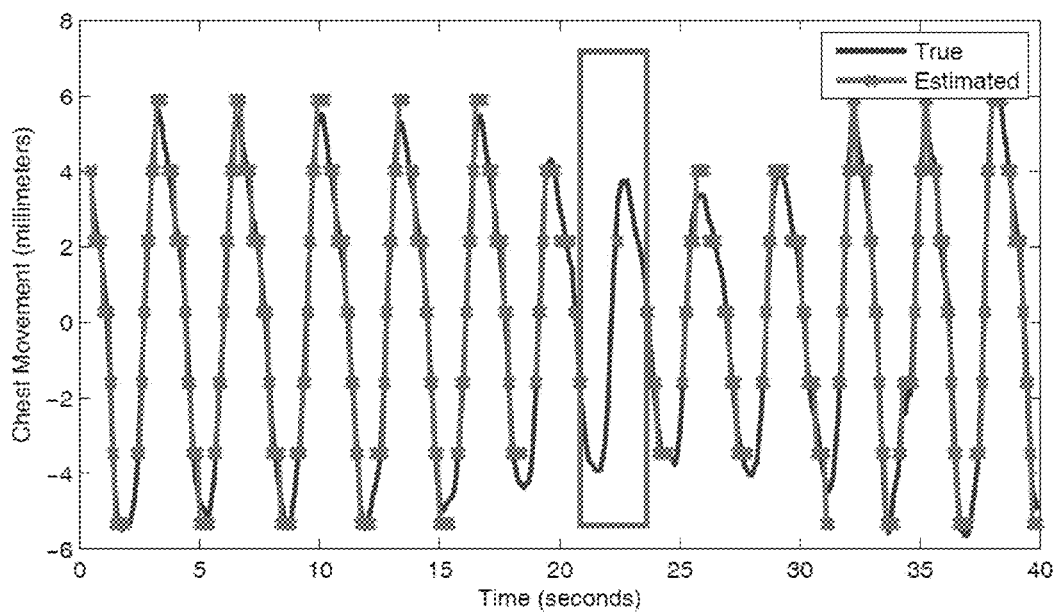
FIG. 20 depicts tracking performance in an environment with a fast-varying background at 15 dB SNR and with a sub-Nyquist sampling rate of 2.1 GHz.

Although FIG. 2 depicts only one patient, the system can be configured to monitor multiple patients simultaneously. Such embodiments can be implemented through the use of multiple transceivers or by configuring a single transceiver component to monitor a wide area or separate and discrete areas. A multi-transceiver system can be implemented in thick client-type configurations that transmit data to a central system and/or through thin client-type configurations. A thin client-type embodiment is shown in FIG. 13. In this embodiment, the system can be separated into several transceiver components, one for each patient, and a separate central processing component. A pulse generator can be disposed in each transceiver or with the central processing component.

A sampler can also be disposed in each transceiver, or it can be disposed with the central processing component.

The respiratory motion of a human includes movement of the chest wall and the abdomen. The chest expands or shrinks as air is taken in and out of the lungs. To monitor the respiratory movements, the UWB transceiver can be directed towards the chest as shown in FIG. 2. The transmitter can emit pulses, at least some of which can be reflected off the chest of the human subject. However, due to multiple paths of travel, these reflections will be superimposed by the reflections of the same pulses off other surfaces and/or objects in the environment, which can create an impulse response that is non-sparse in general.

Impulse response reflected off objects other than the chest of the human subject, called the background, can be more dominant than the components reflected off the chest, which is a signal of interest. It is therefore preferred to eliminate the background before useful information is extracted from the measurements. In the case where the background is assumed known or constant, it can be estimated by averaging measurements over a certain period and subtracting the average from subsequent measurements. However, in practical situations, the background might be unknown and time varying. Hence, a more robust system and method for removing and/or mitigating background effects, as described herein, is needed.

Exemplary embodiments can further include systems and/or techniques to address clock drift, for example, by those developed within the IEEE 802.11 and/or 802.15 standards. Embodiments can further include jitter mitigation, for example, anti jitter circuits, dejitterizers, buffers, and/or filters. By addressing one or both of clock drift and jitter, accuracy and reliability can be improved.

In some embodiments, temperature sensors, for example an infrared temperature sensor, can be included in the system to measure temperature changes in the patient and/or during the cyclic air movement of each breath. The system can further include alarms to notify care givers of significant changes in a patient's respiration. For example, the processor can generate a signal to raise an alarm. The alarm can be triggered when, for example, a non-trivial change in respiration occurs as measured from the amplitude of the ultra-wideband impulse responses and/or as measured from reduction in amplitude of a temperature wave form as the patient reduces their breath-to-breath tidal volume. In other embodiments, rather than simply utilizing the amplitude of the impulse response, the location of the most significant component within the impulse response can be utilized to estimate the chest position.

In some embodiments, the system can include a sensor system for additionally measuring heart rate, blood pressure, and/or blood oxygen levels. The sensor system can include a camera, a Doppler vibrometer, a wireless bio-radar sensor, a spatial diversity diode detector array, and/or equally useful sensors as are known in the art.

An exemplary embodiment can include a sparse signal estimation. The sparse nature of UWB impulse responses can be exploited, for example, to obtain high performance at low SNR values. A sparse matrix, as opposed to a dense matrix, is a matrix populated primarily with elements equal to zero. The sparsity (or density) of a matrix can be described by the fraction of zero elements (non-zero elements) in the matrix. The sparsity of the impulse response can itself be exploited. For example in some embodiments, an impulse response can be estimated and/or recovered by exploiting sparsity of the impulse response.

The technique can utilize a modified multiple pulse transmission technique, which can reduce the required sampling rate. Further, expressions for a single path case can be sufficient for formulation due to the background removal techniques presented herein.

Figure 3:
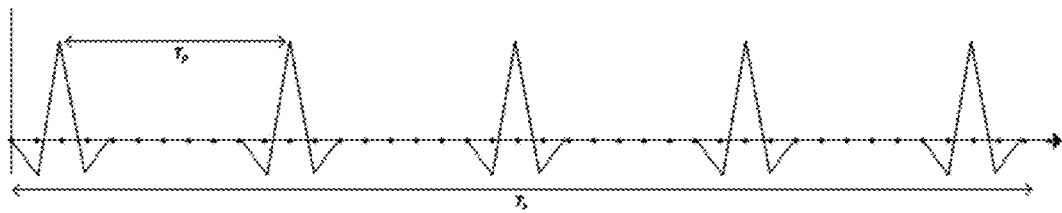
FIG. 3 depicts an exemplary transmitted pulse sequence for SNR improvement.

In typical multi-pulse transmission techniques, the transmitted signal can include a sequence of N pulses as shown in FIG. 3. The train of pulses can be expressed mathematically as $$s(t) = \sum_{k=0}^{N-1} p_{tx}(t - kT_p) \quad (4)$$

All pulses can have duration of time $T_w$ and can be separated by intervals of duration $T_p$. These pulses can be transmitted within a single measurement window of time period $T_s$. Here, $T_p$ is assumed to be greater than $T_w$ and chosen such that the multipaths die out before transmission of the next pulse in the sequence. The transmitted pulse $p_{tx}$ is the second derivative Gaussian pulse as given in (1).

The received pulses will be delayed versions of the transmitted pulses by time $\tau$, which is incurred due to the round-trip distance between the transceiver and the reflecting object. The overall measurement is the average of the reflections over all such transmitted pulses within the $T_s$ time window and can be described by the expression $$y(t) = \frac{1}{N} \sum_{k=0}^{N-1} (g(t - kT_p - \tau) + n(t)) \quad (5)$$

where g(t) is the reflected signal and n(t) is zero-mean white Gaussian noise with variance $\sigma_n^2$.

The general measurement model from the use of such a technique can be expressed using vector-matrix notation as $$y = Ah + n \quad (6)$$

where y is the m×1 measurement vector, A is the measurement matrix of size m×n and n is a vector of size m×1 representing zero-mean white Gaussian noise. h is the sparse vector of size n×1 to be estimated and composed of two parts; $h_c$, representing the impulse response created by the subject's chest movement, and $h_{bc}$, representing the impulse response created by the background objects in the environment. The measurement matrix for the specific transmission technique in (5) has a Toeplitz structure in which each column is a shifted version of the transmitted UWB pulse. This can be denoted by the matrix $$\overline{A} = \begin{bmatrix} p(0) & & & & \\ p(1) & p(0) & & & \\ \vdots & p(1) & \ddots & & \\ p(k-1) & \vdots & \ddots & p(0) & \\ & p(k-1) & & p(1) & \\ & & \ddots & \vdots & \\ & & & p(k-1) \end{bmatrix}$$

where [p(0), p(1), . . . , p(k−1)] are the samples of the transmitted pulse at Nyquist rate.

By modifying the foregoing technique, an exemplary embodiment described herein can allow sampling the received signal at sub-Nyquist frequencies while still achieving the accuracy offered at the Nyquist rate. A key feature of the technique can include utilizing as many pulses in the transmit sequence as the intended amount of subsampling. In other words, for analyzing N pulses, the technique includes subsampling by a factor of N compared to the Nyquist rate. The received sequence can then be the delayed version of the transmitted pulse sequence. Unlike prior techniques where averaging at the receiver over multiple pulses is performed, the present technique can allow subsampling the received sequence by a factor of N. Moreover, prior schemes utilizing averaging are generally adopted to improve recovery of signal at low SNR levels, and have not been used or modified as described herein for addressing sampling rates. Under the condition that the pulse interval $T_p$ is proportional to mN−1, where m is any integer, recovering the same samples as when sampling a single pulse with the Nyquist rate, albeit with different permutation, can be assured. Specifically, $L_p$ can be defined as $L_p=T_p f_N$, where $f_N$ is the proportionality constant such that $L_p=T_p f_N=mN-1$. In one aspect, the technique can utilize multiple pulses to recover the same information that would effectively be carried by a single pulse, and resultantly, the requirement on the sampling rate at the receiver side, which is the main bottleneck in any high-frequency system, can be relaxed. The condition $L_p=mN-1$ can ensure that the samples are taken from unique locations from each of the received multiple pulses and can easily be satisfied because of $T_p$ being a flexible design parameter. The transmission technique subject to the condition can be described by the mathematical expressions $$s(t) = \sum_{k=0}^{N-1} p_{tx}(t - kT_p) \text{ s.t. } L_p = T_p f_N = mN - 1 \qquad (7)$$

The resulting measurement, y(t), can be constructed by concatenating the received sequence over all N transmitted pulses and subsampling it by a factor of N. Mathematically, this can be expressed as $$y(t) = \left[ \sum_{k=0}^{N-1} (g(t - kT_p - \tau) + n(t)) \right]_{\downarrow N} \qquad (8)$$

where ↓ N denotes subsampling by a factor of N and the delay, τ, is defined by the distance of the reflecting object from the transceiver as before.

Figure 4:
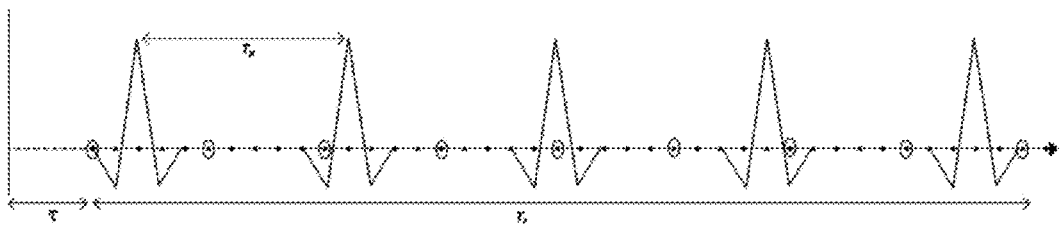
FIG. 4 depicts an exemplary illustration of pulse sample recovery by subsampling of a received sequence.

Recovery of pulse samples from a received sequence using the subsampling approach is illustrated in FIG. 4 for N=5. Here, $L_p$=9 which satisfies the condition given above. The circled points are the sampling instances according to the subsampling ratio N=5 and it can be seen that all the required samples can be recovered from the pulses in the received sequence. The signal model can also be represented in the form of (6) with the difference in the formulation of the measurement matrix Ã whose columns are the subsampled and shifted versions of the transmitted pulse sequence in (7), i.e.

$$a_j = [s(t-(j-1)\delta t_s)]_{\downarrow N}$$

where $a_j$ is the jth column of matrix Ã with j=1, 2, ..., n and $\delta t_s$ is the sampling interval defined by the Nyquist sampling rate for the transmitted pulses.

The received signal, y(t), can comprise several multipath components of which only one component is assumed to be reflected off the chest of the human subject. This component of the measurement signal can provide information about the impulse response, $h_c(t)$, related to the subject's chest movements. All remaining multipath components correspond to the impulse response created by objects other than the human subject's chest and/or abdomen, such as beds, chairs, walls, and other parts of the patient's body. They can be represented as $h_{bc}(t)$. Equation (6) can hence be written as $$y = A(h_c + h_{bc}) + n \qquad (9)$$

The background component can be time variant but is assumed to remain constant over short time durations such as the duration between two measurements. The impulse response, $h_c(t)$, can vary in time as a result of being modulated by the subject's chest movements. Tracking variations in $h_c(t)$ can facilitate tracking variations in chest displacements.

Under the assumption that the background remains substantially constant between any two consecutive measurements, undesired signal components can be eliminated, for example, by using the difference between two consecutively received signals. The difference between the two measurements can be expected to cancel out effects of multipath components, retaining only the signal of interest, $h_c(t)$. The signal of interest would not cancel out due to the subject's chest movements.

It should be noted that while the background can remain substantially constant during most measurement times, which can validate the assumption $h_{bc}(t-\delta t_b)=h_{bc}(t)$, at specific instances when the assumption fails, the algorithm might momentarily fail to track respiration. As the background environment stabilizes, tracking can be resumed. Importantly, a brief loss of tracking can by itself provide useful measurable information regarding movements of the patient. For example, patient movements of interest can result from the mundane, such as awaking or tossing and turning, to the more serious, such as convulsing or respiratory arrest/death events. Recordation of disturbances in sleeping patterns, in addition to respiration patterns, is an important parameter of sleep apnea studies. Monitoring for more serious conditions can provide early warning signals to medical professionals and/or first responders.

The mathematical expression resulting from using equation (9) with N=1 is given by $$z = y_{t-\delta t_b} - y_t = A(h_{t-\delta t_b} - h_t) - n_{t-\delta t_b} - n_t \qquad (10)$$

where $\delta t_b$ represents the interval between any two consecutive measurements. Let $$n_{t-\delta t_b} - n_t = m_t$$

Then, $$z_t = A(h_{bc(t-\delta t_b)} + h_{c(t-\delta t_b)} - \{h_{bc(t)} + h_{c(t)}\}) + m_t \qquad (11)$$

For $\delta t_b < 1$ second, $h_{bc(t-\delta t_b)} = h_{bc(t)}$ and hence $$z_t = A h_{d(t)} + m_t \qquad (12)$$

with $h_{d(t)} = h_{c(t-\delta tb)} - h_{c(t)}$, in other words, the differential impulse response.

In some embodiments, a greedy algorithm, such as support agnostic Bayesian matching pursuit (SABMP), algorithm can be utilized. Greedy algorithms are a class of heuristic techniques that can be designed to quickly find locally optimal solutions with the goal of finding a global optimum more quickly, i.e. with less computational expense, than classical or direct methods. The techniques generally follows a problem solving heuristic of making the locally optimal choice at each step with the hope of finding a global optimum. Often, a greedy strategy may not produce the optimal solution, but nonetheless yields locally optimal solutions that approximate a globally optimal solution.

As discussed above, sparsity implies that the vector to be estimated can be expected to have only a few non-zero elements. After the removal of the multipath effects, the remaining impulse response, $h_{c(t)}$, is a sparse vector with the locations of nonzero elements dependent on the current location of the chest. Several greedy algorithms have been developed for sparse signal estimation. Algorithms like orthogonal matching pursuit (OMP) can operate based only on the sparsity information without considering any signal or noise characteristics. Other algorithms, like fast Bayesian matching pursuit (FBMP) and SABMP, can use Bayesian statistics of the signal and noise, along with sparsity rate, to compute the sparse vector estimate.

Although other algorithms can be utilized, SABMP has an advantage in that it does not make an assumption on the distribution of the signal to be estimated, which makes it suitable for applications where signal statistics might be unknown. The noise can be assumed to be Gaussian, which can be a reasonable assumption in most cases. The initial estimate of sparsity provided to the algorithm can be refined after each greedy search for the estimation of the sparse vector.

The minimum mean square error (MMSE) estimate in the SABMP algorithm can be given by the expression $$\hat{h}_{mmse} \triangleq E[h|y] = \sum_S ;(S|y)E[h|y,S] \qquad (13)$$

where h is the sparse vector to be estimated with unknown distribution of the non-zero elements and y is the set of available observations. The sum is over all possible $2^n$ supports S, where n is the dimension of h. This means that the SABMP algorithm can explore the entire dimension, n, of the vector to be estimated to provide the MMSE solution. Moreover, the SABMP algorithm can outperform many other algorithms in speed and estimation accuracy.

Input arguments to the algorithm can include the differential measurement vector, z, the measurement matrix, A, a parameter, $r_{stop}$, which defines the refinement limit, and an initial estimate of the sparsity rate, p. Other known algorithmic parameters need not be discussed here but can be included as result-effective variables.

The signal model aspects of exemplary embodiments discussed above can provide a means for obtaining impulse responses created by the interaction of the UWB pulse with the chest and/or abdomen of the human subject. After background removal, the remaining impulse response, $h_c(t)$, can include a single cluster of non-zero taps and can be modeled as a sparse vector. The locations of these non-zero elements within the sparse vector carry information on the round-trip delay, which can be dependent on the current distance of the chest from the ultra-wideband transceiver. Respiratory movements can induce a variable path delay for the reflected pulse and hence the location of these non-zero elements can move up and down periodically under the transceiver schematically shown in FIG. 2. By estimating this sparse vector and the locations of the non-zero elements (or more specifically that of the largest element) in it, movements of the chest and/or abdomen can be tracked and the respiratory signal can be estimated. The SABMP algorithm, for example, can be employed for estimating the sparse vector, $h_c(t)$, and obtaining delay information using the expression $$\tau = \arg \max(h_c[i]) \qquad (14)$$

where i is the index of the vector locations from 1 to n.

Time delay information can be used to obtain the current distance of the chest wall from the transceiver, for example, by using $$d = \frac{\tau c}{2 f_N} \qquad (15)$$

Here, the sampling frequency used is defined by the Nyquist criterion, $f_N$, and not the sub-Nyquist frequency, $f_S$, at which the received signal is actually sampled.

An exemplary embodiment of the method can include a respiratory movement tracking algorithm. The technique can include transmitting a sequence of N pulses, subject to the condition that $L_p=mN-1$ where N is the desired subsampling ratio and m is any integer. The technique can include receiving and subsampling y(t) at $f_S=f_N/N$ over the $T_s$ measurement time window. The differential signal, $z_t=Ah_d$ $(t)+m_t$ can be calculated. The impulse response, $h_c$, can be estimated, for example, using the SABMP algorithm. The time of flight, $\tau$, of signals transmitted from a transceiver and reflected or scattered back to the transceiver can be estimated. Further, the technique can include calculating the chest wall position, d, in order to measure and monitor respiration of a patient.

Figure 5:
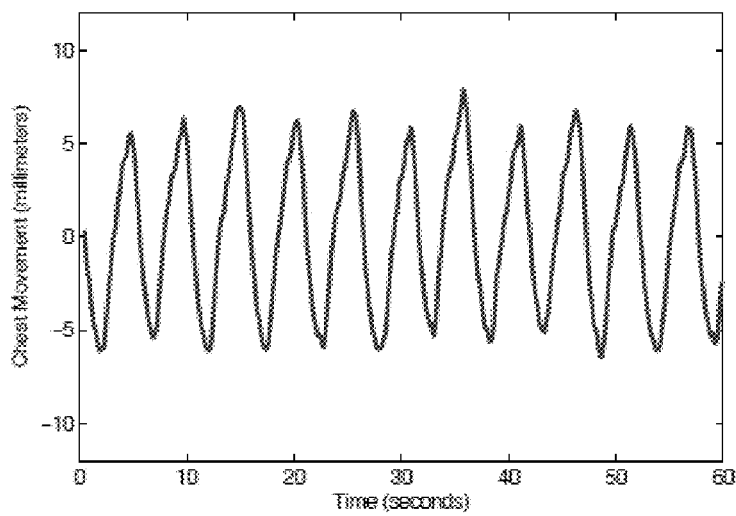
FIG. 5 depicts an exemplary pre-recorded respiratory signal.

FIGS. 5-12 and 14-20 depict various aspects and data associated with the performance of exemplary embodiments. FIG. 5 shows the plot of a signal associated with respiration. The recorded data in FIGS. 5-9 represent normal respiratory movements of a human subject having a duration of 60 seconds. FIGS. 14-20 represent normal respiratory movements over a 40-second duration. The recordings were taken while the subject was asleep. The signal plotted in FIG. 5 can be used to modulate the transmitted sequence to generate the synthetic measurements.

The embodiment can utilize, for example, an IEEE 802.15.3a UWB channel transceiver. Qualitative performance of the technique can be analyzed by the quality of signal waveform reconstruction, which can be useful for physician to detect abnormal breathing patterns. The quantitative performance can be measured in terms of the root mean-square-error (RMSE) defined as $$\text{RMSE} = \sqrt{E((\hat{d})-d)^2} \qquad (16)$$

where $\hat{d}$ is the estimated and d is the true position of the chest.

Figure 6:
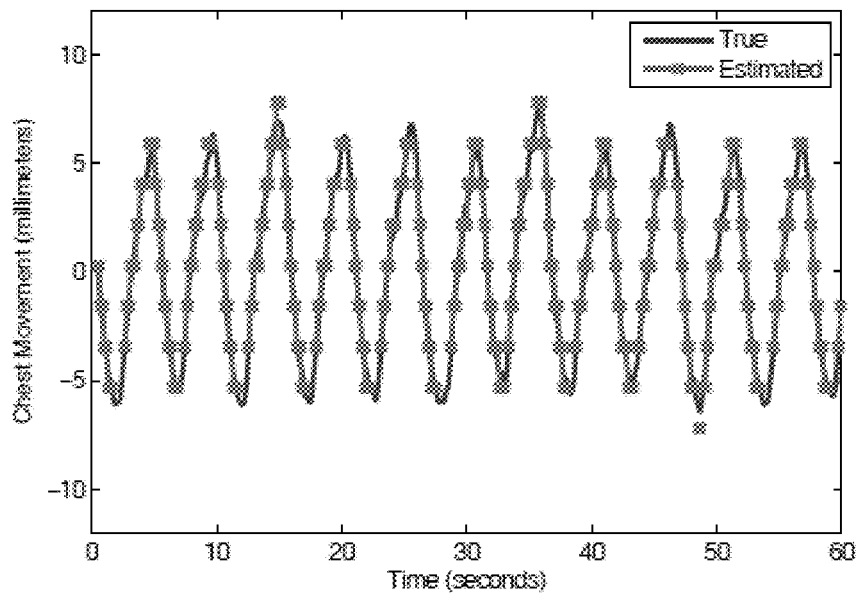
FIG. 6 depicts signal reconstruction performance at 15 dB SNR with a Nyquist sampling rate of 80 GHz.
Figure 7:
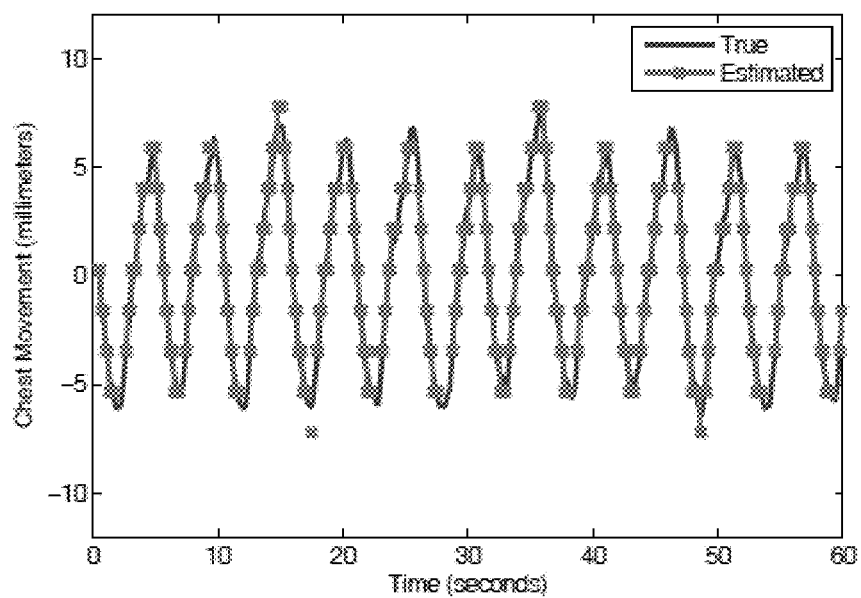
FIG. 7 depicts signal reconstruction performance at 15 dB SNR with a sub-Nyquist sampling rate of 2.1 GHz.

FIG. 6 shows the tracking performance at the Nyquist sampling rate. The signal can exhibit peak-to-peak amplitudes of approximately 11 mm and the range resolution, $\delta r$, can be set to 2 mm, which can be achieved using a pulse width, $T_w$, of 50 picoseconds with the associated Nyquist sampling rate being 80 GHz. The estimated signal shows good tracking performance, achieving a range resolution, $\delta r$, of 2 mm offered by the utilized pulse width. Higher resolutions can be also be obtained by using finer pulses. Such a range is sufficient for qualitative analysis. As discussed above, sampling the received signal at the Nyquist rate can be computationally expensive. However, with the exemplary embodiment, the same Nyquist rate performance can be achieved while sampling at a much lower rate. For example, sampling rates of $f_S=2.1$ GHz with N=37 can be used in the transmit sequence of equation (7). FIG. 7 shows the tracking performance for such a subsampled case, which is very similar to the results shown in FIG. 6.

Figure 8:
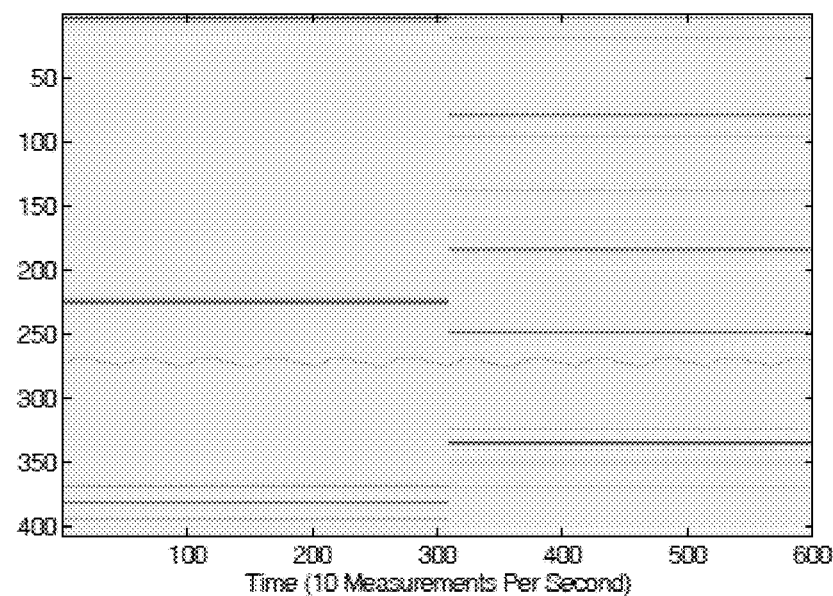
FIG. 8 depicts measurement vectors in an environment with a changing background.
Figure 9:
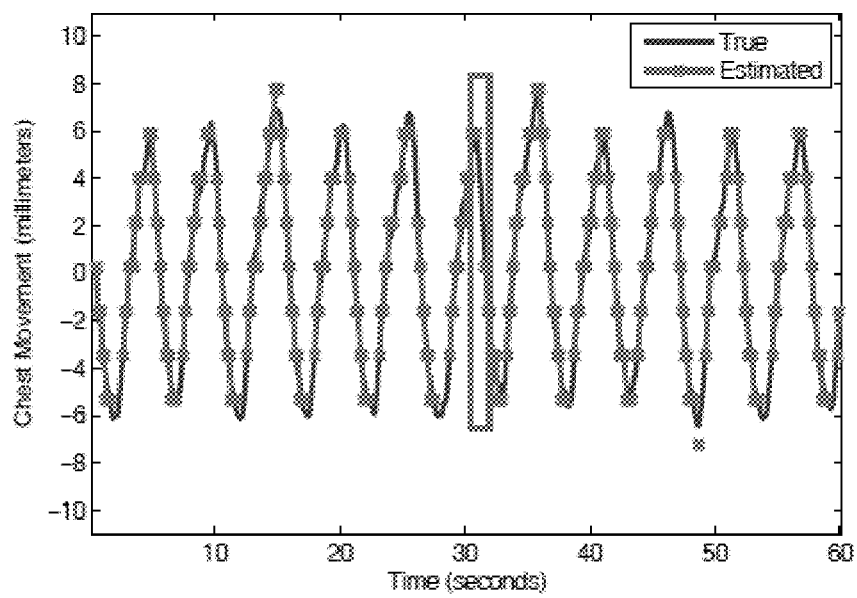
FIG. 9 depicts performance in an environment with a time-varying background at 15 dB SNR and with a sub-Nyquist sampling rate of 2.1 GHz

A simulated time-variant background environment can be utilized to evaluate the performance of background removal. FIG. 8 shows a collection of measurement vectors, y, over time where the background environment changes abruptly around time t=32 seconds. The tracking performance of the algorithm is shown in FIG. 9 where it can be seen that the algorithm loses track of the respiratory movements for a short duration around the time of change in the background environment. The system, as shown, is able to regain tracking as soon as the environment stabilizes.

Figure 10:
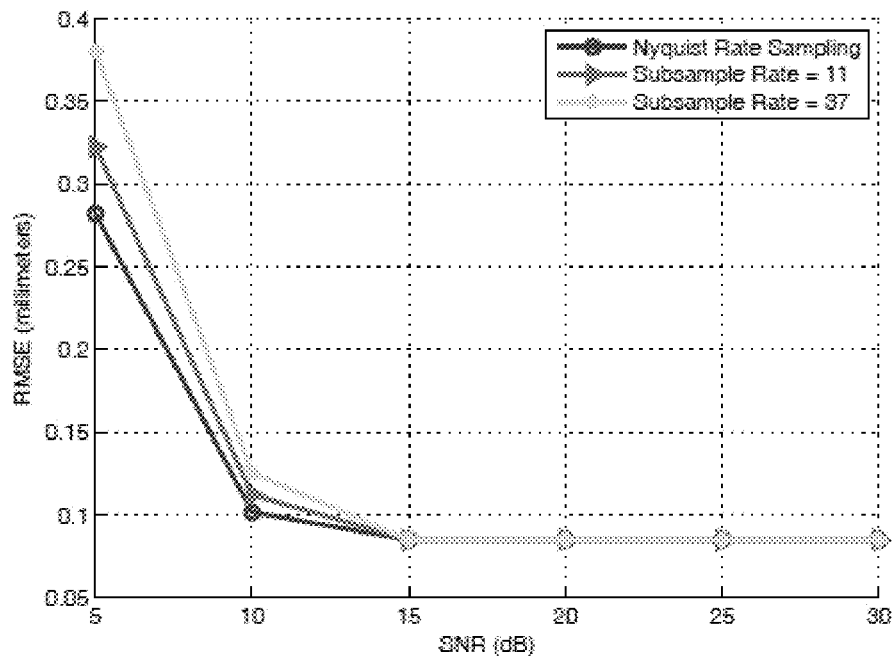
FIG. 10 depicts a root mean-square-error (RMSE) comparison between Nyquist and sub-Nyquist sampling rates.

A quantitative analysis of the technique can be conducted. FIG. 10 plots the RMSE for the subsampled case compared with that of the Nyquist rate sampling. The subsampled technique, as shown in the figures, performs well for SNR values above 8 dB with an RMSE of around 0.5 mm with the range resolution given above.

Figure 11:
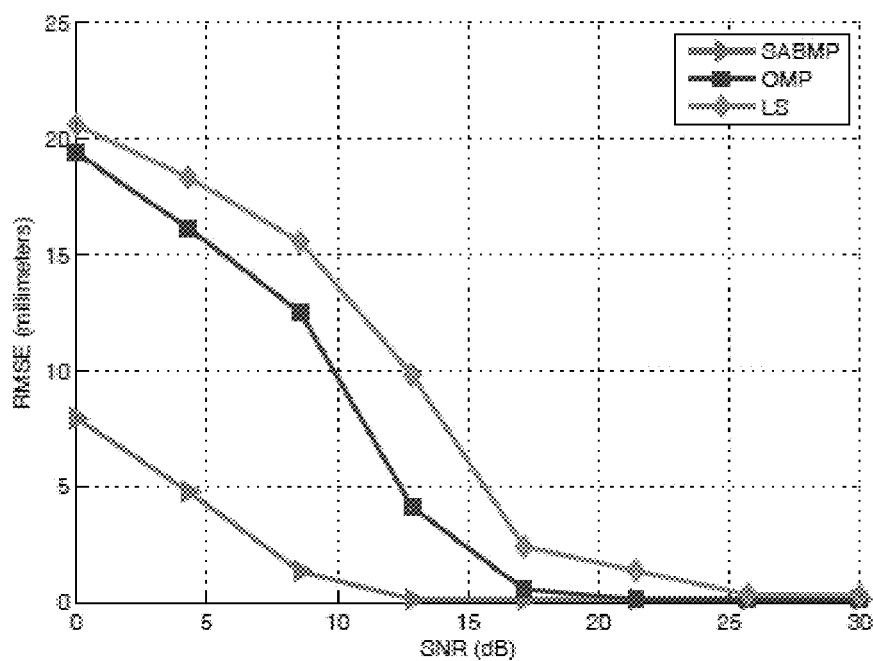
FIG. 11 depicts a performance comparison with non-sparsity based least squares (LS) and sparse non-Bayesian orthogonal matching pursuit (OMP) algorithms at the Nyquist rate.
Figure 12:
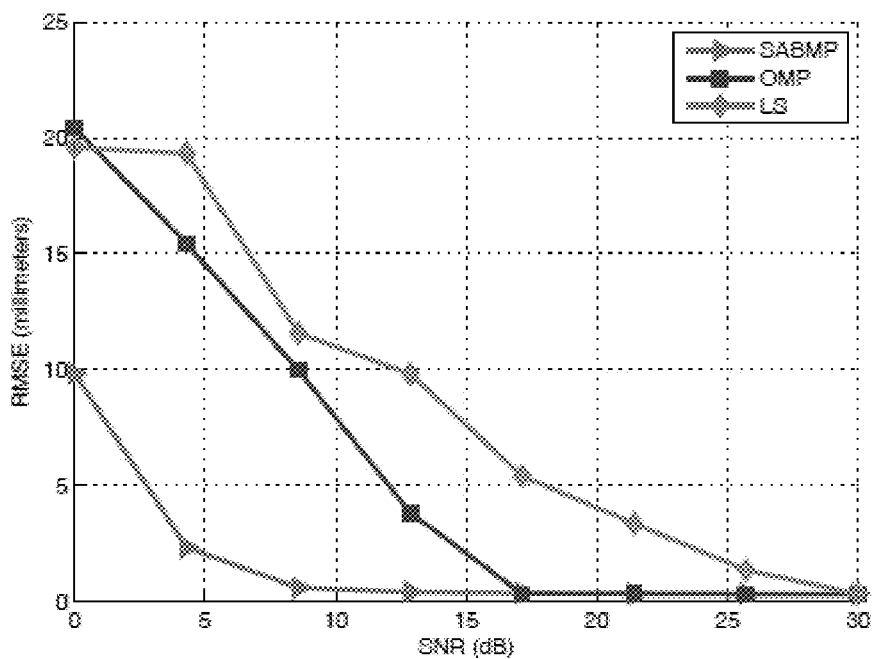
FIG. 12 depicts a performance comparison with non-sparsity based LS and sparse non-Bayesian OMP algorithms at a sub-Nyquist rate.

FIGS. 11 and 12 show the performance enhancement attributed to the sparse signal estimation approach of embodiments that include the Bayesian framework of the SABMP algorithm compared to alternative embodiments that include OMP and Least Squares (LS) methods. Specifically, in FIGS. 11 and 12, the RMSE for both the Nyquist and sub-Nyquist cases against SNR values in the range of 0 to 30 dB are plotted. The enhanced performance from the SABMP algorithm, which exploits both the sparsity and the Bayesian estimation framework, shows its usefulness as it achieves the minimum RMSE value at a much lower SNR compared with both the LS and OMP methods.

The steps of estimating the UWB channel impulse response and dynamically removing clutter can allow dealing with multipath issues in an effective and simple manner. Accurate tracking of respiratory rate as well as the respiratory amplitude in a non-isolated and time variant background environment can be achieved. Exemplary embodiments exploiting sparsity and recovering information from signals at low signal-to-noise ratios can provide extremely good performance in harsh operating environments. Moreover utilizing a multiple pulse transmission technique allows recovery of received signals while operating at frequencies much lower than the Nyquist requirement. Being able to recover signals while operating at sub-Nyquist frequencies reduces the complexity of the hardware involved thus enabling the development of a low-cost commercial product.

The embodiments may take the form of a hardware embodiment, a software embodiment, or an embodiment combining software and hardware. In one embodiment, the present invention takes the form of a computer-program product that includes computer-useable instructions embodied on one or more computer-readable media.

The various integrated techniques, methods, and systems described herein can be implemented in part or in whole using computer-based systems and methods. Additionally, computer-based systems and methods can be used to augment or enhance the functionality described herein, increase the speed at which the functions can be performed, and provide additional features and aspects as a part of or in addition to those described elsewhere in this document. Various computer-based systems, methods and implementations in accordance with the described technology are presented below.

Embodiments may include a general-purpose computer and can have an internal or external memory for storing data and programs such as an operating system (e.g., DOS, Windows 2000™, Windows XP™, Windows NT™, OS/2, UNIX or Linux) and one or more application programs. Examples of application programs include computer programs implementing the techniques described herein for lyric and multimedia customization, authoring applications (e.g., word processing programs, database programs, spreadsheet programs, or graphics programs) capable of generating documents or other electronic content; client applications (e.g., an Internet Service Provider (ISP) client, an e-mail client, or an instant messaging (IM) client) capable of communicating with other computer users, accessing various computer resources, and viewing, creating, or otherwise manipulating electronic content; and browser applications (e.g., Microsoft's Internet Explorer) capable of rendering standard Internet content and other content formatted according to standard protocols such as the Hypertext Transfer Protocol (HTTP). One or more of the application programs can be installed on the internal or external storage of the general-purpose computer. Alternatively, in another embodiment, application programs can be externally stored in or performed by one or more device(s) external to the general-purpose computer.

The general-purpose computer may include a central processing unit (CPU) for executing instructions in response to commands, and a communication device for sending and receiving data. One example of the communication device is a modem. Other examples include a transceiver, a communication card, an antenna, a network adapter, or some other mechanism capable of transmitting and receiving data over a communications link through a wired or wireless data pathway.

The general-purpose computer may also include an input/output interface that enables wired or wireless connection to various peripheral devices. Examples of peripheral devices include, but are not limited to, a mouse, a mobile phone, a personal digital assistant (PDA), a keyboard, a display monitor with or without a touch screen input, and an audiovisual input device. In another implementation, the peripheral devices may themselves include the functionality of the general-purpose computer. For example, the mobile phone or the PDA may include computing and networking capabilities and function as a general purpose computer by accessing a network and communicating with other computer systems. Examples of a network that can be utilized to implement various embodiments include the Internet, the World Wide Web, WANs, LANs, analog or digital wired and wireless telephone networks (e.g., Public Switched Telephone Network (PSTN), Integrated Services Digital Network (ISDN), and Digital Subscriber Line (xDSL)), radio, television, cable, or satellite systems, and other delivery mechanisms for carrying data. A communications link can include communication pathways that enable communications through one or more networks.

In one implementation, a processor-based system of the general-purpose computer can include a main memory, preferably random access memory (RAM), and can also include a secondary memory. The secondary memory can include, for example, a hard disk drive or a removable storage drive, representing a floppy disk drive, a magnetic tape drive, an optical disk drive (Blu-Ray, DVD, CD drive), magnetic tape, paper tape, punched cards, standalone RAM disks, Iomega Zip drive, etc. The removable storage drive can read from or write to a removable storage medium. A removable storage medium can include a floppy disk, magnetic tape, optical disk (Blu-Ray disc, DVD, CD) a memory card (CompactFlash card, Secure Digital card, Memory Stick), paper data storage (punched card, punched tape), etc., which can be removed from the storage drive used to perform read and write operations. As will be appreciated, the removable storage medium can include computer software or data.

In alternative embodiments, the secondary memory can include other similar means for allowing computer programs or other instructions to be loaded into a computer system. Such means can include, for example, a removable storage unit and an interface. Examples of such can include a program cartridge and cartridge interface (such as the found in video game devices), a removable memory chip (such as an EPROM or PROM) and associated socket, and other removable storage units and interfaces, which allow software and data to be transferred from the removable storage unit to the computer system.

In one embodiment, a network can include a communications interface that allows software and data to be transferred between client devices, central servers, and other components. Examples of communications interfaces can include a modem, a network interface (such as, for example, an Ethernet card), a communications port, and a PCMCIA slot and card. Software and data transferred via a communications interface may be in the form of signals, which can be electronic, electromagnetic, optical or other signals capable of being received by a communications interface. These signals may be provided to a communications interface via a channel capable of carrying signals and can be implemented using a wireless medium, wire or cable, fiber optics or other communications medium. Some examples of a channel can include a phone line, a cellular phone link, an RF link, a network interface, and other suitable communications channels.

In this document, the terms "computer program medium" and "computer readable medium" are generally used to refer to media such as a removable storage device, a disk capable of installation in a disk drive, and signals on a channel. These computer program products may provide software or program instructions to a computer system.

Computer-readable media include both volatile and non-volatile media, removable and non-removable media, and contemplate media readable by a database, a switch, and various other network devices. Network switches, routers, and related components are conventional in nature, as are means of communicating with the same. By way of example, and not limitation, computer-readable media include computer-storage media and communications media.

Computer-storage media, or machine-readable media, include media implemented in any method or technology for storing information. Examples of stored information include computer-useable instructions, data structures, program modules, and other data representations. Computer-storage media include, but are not limited to RAM, ROM, EEPROM, flash memory or other memory technology, CD-ROM, DVD, holographic media or other optical disc storage, magnetic cassettes, magnetic tape, magnetic disk storage, and other magnetic storage devices. These memory components can store data momentarily, temporarily, or permanently.

Communications media typically store computer-useable instructions—including data structures and program modules—in a modulated data signal. The term "modulated data signal" refers to a propagated signal that has one or more of its characteristics set or changed to encode information in the signal. An exemplary modulated data signal includes a carrier wave or other transport mechanism. Communications media include any information-delivery media. By way of example but not limitation, communications media include wired media, such as a wired network or direct-wired connection, and wireless media such as acoustic, infrared, radio, microwave, spread-spectrum, and other wireless media technologies. Combinations of the above are included within the scope of computer-readable media.

In an embodiment where the elements are implemented using software, the software can be stored in, or transmitted via, a computer program product and loaded into a computer system using, for example, a removable storage drive, hard drive or communications interface. The control logic (software), when executed by the processor, may cause the processor to perform the functions of the techniques described herein.

In another embodiment, the elements may be implemented primarily in hardware using, for example, hardware components such as PAL (Programmable Array Logic) devices, application specific integrated circuits (ASICs), or other suitable hardware components. Implementation of a hardware state machine so as to perform the functions described herein will be apparent to a person skilled in the relevant art(s). In yet another embodiment, elements may be implanted using a combination of both hardware and software.

In another embodiment, the computer-based methods can be accessed or implemented over the World Wide Web by providing access via a Web Page to the methods described herein. Accordingly, the Web Page may be identified by a Universal Resource Locator (URL). The URL may denote both a server and a particular file or page on the server.

Each of the following references is hereby incorporated by reference in its entirety.

National Heart, Lung and Blood Institute, U.S. Department of Health and Human Services; "What Is Sleep Apnea?"

National Health Services, UK; "Diagnosing Sleep Apnea."

E. M. Staderini; "UWB Radars in Medicine", Aerospace and Electronic Systems Magazine, IEEE, vol. 17, no. 1, pp. 13-18, January 2002.

H. Soganci, S. Gezici, O. Arikan; "A Bayesian approach to respiration rate estimation via pulse-based ultra-wideband signals", Ultra-Wideband, 2009. ICUWB 2009. IEEE International Conference on, 9-11 Sep. 2009.

S. Gezici; "Theoretical Limits for Estimation of Periodic Movements in Pulse-Based UWB Systems", Selected Topics in Signal Processing, IEEE Journal of, vol. 1, no. 3, pp. 405-417, October 2007.

A. Lazaro, D. Girbau, R. Villarino, A. Ramos; "Vital signs monitoring using impulse based UWB signal", Microwave Conference (EuMC), 2011 41st European, 10-13 Oct. 2011.

J. C. Y. Lai, Y. Xu, E. Gunawan, E. C. Chua, A. Maskooki, Y. L. Guan, K. Low, C. B. Soh, C. Poh; "Wireless Sensing of Human Respiratory Parameters by Low-Power Ultra-wideband Impulse Radio Radar", Instrumentation and Measurement, IEEE Transactions on, vol. 60, no. 3, pp. 928-938, March 2011.

D. Dardari, A. Conti, U. Ferner, A. Giorgetti, M. Z. Win; "Ranging With Ultrawide Bandwidth Signals in Multipath Environments", Proceedings of the IEEE, vol. 97, no. 2, pp. 404, 426, February 2009.

Y. Nijsure, W. Tay, E. Gunawan, F. Wen, Y. Zhang, Y. Guan, A. Chua; "An Impulse Radio Ultra Wideband System for Contactless Non-invasive Respiratory Monitoring", Biomedical Engineering, IEEE Transactions on, vol. 60, no. 6, pp. 1509, 1517, June 2013.

S. Wu, Q. Zhang, R. Fan, N. Zhang, "Match-Filtering Based TOA Estimation for IR-UWB Ranging Systems", Wireless Communications and Mobile Computing Conference, 2008. IWCMC '08. International, 6-8 Aug. 2008

X. Li, K. Pahlavan, J. Beneat; "Performance of TOA estimation techniques in indoor multipath channels", Personal, Indoor and Mobile Radio Communications, 2002. The 13th IEEE International Symposium on, vol. 2, no., pp. 911, 915 vol. 2, 15-18 Sep. 2002

M. G. Di Benedett; "Ultra-wideband Communication Systems: A Comprehensive Overview:", EURASIP Book Series on Signal Processing and Communications, vol 5, 2006.

L. Yang, G. B. Giannakis; "Ultra-wideband communications: an idea whose time has come", Signal Processing Magazine, IEEE, vol. 21, no. 6, pp. 26, 54, November 2004.

G. Ossberger, T. Buchegger, E. Schimback, A. Stelzer, R. Weigel; "Non-invasive respiratory movement detection and monitoring of hidden humans using ultra wideband pulse radar", Ultra Wideband Systems, 2004. Joint with Conference on Ultrawideband Systems and Technologies. Joint UWBST & IWUWBS. 2004 International Workshop on, 18-21 May 2004.

Y. C. Pati, R. Rezaiifar, P. S. Krishnaprasad; "Orthogonal matching pursuit: recursive function approximation with applications to wavelet decomposition", Signals, Systems and Computers, 1993. 1993 Conference Record of The Twenty-Seventh Asilomar Conference on, 1-3 Nov. 1993

P. Schniter, L. C. Potter, J. Ziniel, "Fast bayesian matching pursuit", Information Theory and Applications Workshop, 2008, Jan. 27, 2008-Feb. 1, 2008.

Masood, Mudassir; Al-Naffouri, Tareq Y, "Sparse Reconstruction Using Distribution Agnostic Bayesian Matching Pursuit," IEEE Transactions on Signal Processing, Nov. 1, 2013, Volume 61 Issue 21, pp 5298-5309.

M. Masood and T. Y. Al-Naffouri, "Support Agnostic Bayesian Matching Pursuit for Block Sparse Signals", IEEE International Conference on Acoustics, Speech and Signal Processing (ICASSP 2013), Vancouver, Canada, May 2013.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope or the invention. In addition, from the foregoing it will be seen that this invention is one well adapted to attain all the ends and objects set forth above, together with other advantages. It will be understood that certain features and sub-combinations are of utility and may be employed without reference to other features and sub-combinations. This is contemplated and within the scope of the appended claims. All such similar substitutes and modifications apparent to those skilled in the art are deemed to be within the spirit and scope of the invention as defined by the appended claims.

What is claimed is:

1. A monitoring system for assessing one or more patients, comprising:
   a pulse generator configured to generate ultra-wideband pulses;
   an ultra-wideband transceiver for transmitting the ultra-wideband pulses toward the one or more patients and receiving ultra-wideband signals from the one or more patients, wherein the ultra-wideband pulses have a Nyquist sampling rate;
   a sampler for sampling the ultra-wideband signals at a sample rate less than the Nyquist sampling rate; and
   a processor in communication with the sampler, wherein the processor is configured to monitor one or more biological functions in a non-isolated and time variant environment and to reconstruct a breathing waveform from the ultra-wideband signals based on an agnostic Bayesian matching pursuit algorithm.

2. The system of claim 1, wherein the processor is configured to analyze a number of sampled pulses.

3. The system of claim 2, wherein the number of sampled pulses is substantially equivalent to the ratio of the Nyquist sampling rate to the sample rate.

4. The system of claim 1, wherein the ultra-wideband pulses are separated by a time interval of $T_p$ and wherein a subsampling ratio, N, conforms with $T_p f_N = mN-1$, where m is an integer and $f_N$ is the Nyquist sampling rate.

5. The system of claim 4, wherein the processor is configured to execute a greedy algorithm to estimate an impulse response based on sparsity of the impulse response.

6. The system of claim 1, wherein the processor is configured to monitor one or more biological functions in a non-isolated and time variant environment.

7. The system of claim 6, wherein the one or more biological functions comprise respiration.

8. The system of claim 7, wherein the one or more biological functions comprise heart rate.

9. The system of claim 7, wherein the processor is configured to monitor movement.

10. A method of wirelessly monitoring one or more patients, comprising:
    transmitting ultra-wideband pulses toward the one or more patients;
    receiving ultra-wideband signals, wherein the ultra-wideband pulses have a Nyquist sampling rate;
    sampling the ultra-wideband signals at a sample rate less than the Nyquist sampling rate;
    calculating a differential signal and removing time-varying background clutter; and
    reconstructing a breathing waveform from the ultra-wideband signals based on an agnostic Bayesian matching pursuit algorithm.

11. The method of claim 10, further comprising analyzing a number of sampled pulses.

12. The method of claim 11, wherein the number of sampled pulses is substantially equivalent to the ratio of the Nyquist sampling rate to the sample rate.

13. The method of claim 10, wherein the ultra-wideband pulses are separated by a time interval of $T_p$ and wherein a subsampling ratio, N, conforms with $T_p f_N = mN-1$, where m is an integer and $f_N$ is the Nyquist sampling rate.

14. The method of claim 13, further comprising executing a greedy algorithm to estimate an impulse response based on sparsity of the impulse response.

15. The method of claim 13, further comprising calculating a differential signal and removing time-varying background clutter.

16. The method of claim 15, further comprising estimating an impulse response.

17. The method of claim 16, wherein the ultra-wideband signals are reflections of the ultra-wideband pulses, further comprising estimating a time of travel of the ultra-wideband pulses.

18. The method of claim 17, further comprising calculating a position as a function of time to determine one or more biological functions.

19. The method of claim 15, wherein the differential signal is a difference between a measurement at a current time instance and an earlier time instance.

20. The method of claim 10, further comprising monitoring one or more biological functions.

21. The method of claim 20, wherein the one or more biological functions comprise respiration.

22. The method of claim 21, wherein the one or more biological functions comprise heart rate.

23. The method of claim 21, further comprising monitoring movement.

24. The system of claim 1, wherein the processor is configured to reconstruct a breathing waveform.

25. A computer having a non-transitory computer readable medium comprising a program for monitoring at least one patient and configured to execute:
   transmitting to the at least one patient a sequence of N pulses having a period of $T_p$ and a Nyquist sampling rate;
   receiving signals based on the sequence of N pulses;
   subsampling the signals at a sample rate, wherein the sample rate is defined by the Nyquist sampling rate reduced by a factor of N and wherein N conforms to $T_p f_N = mN-1$, where m is an integer and $f_N$ is the Nyquist sampling rate; and
   reconstructing a breathing waveform from the signals based on an agnostic Bayesian matching pursuit algorithm.

26. The computer of claim 25, wherein the program further executes:
   removing time-varying background clutter;
   estimating an impulse response; and
   tracking respiratory movement.

27. The computer of claim 26, wherein the sequence of N pulses comprises ultra-wideband pulses.

28. The computer of claim 26, wherein the sequence of N pulses comprises ultrasonic pulses.

29. The computer of claim 26, wherein the program is further configures to track the respiratory movement while the at least one patient is in a non-isolated and time variant environment.

* * * * *